United States Patent
Park et al.

(10) Patent No.: US 7,709,243 B2
(45) Date of Patent: May 4, 2010

(54) BIOCHIP AND BIOMOLECULAR DETECTION SYSTEM USING THE SAME

(75) Inventors: Young-jun Park, Suwon-si (KR); Jong-min Kim, Suwon-si (KR); Sung-kee Kang, Seongnam-si (KR); Jung-woo Kim, Yongin-si (KR)

(73) Assignee: Samsung SDI Co., Ltd., Suwon (KR)

( * ) Notice: Subject to any disclaimer, the term of this patent is extended or adjusted under 35 U.S.C. 154(b) by 1059 days.

(21) Appl. No.: 11/056,234

(22) Filed: Feb. 14, 2005

(65) Prior Publication Data
US 2005/0181409 A1    Aug. 18, 2005

(30) Foreign Application Priority Data
Feb. 14, 2004    (KR) ............... 10-2004-0009837

(51) Int. Cl.
- C12M 1/00 (2006.01)
- C12M 1/34 (2006.01)
- C12Q 1/00 (2006.01)
- C12Q 1/68 (2006.01)

(52) U.S. Cl. .................... 435/283.1; 435/4; 435/6; 435/7.1; 435/287.2; 977/742; 977/745; 977/746; 977/747; 977/748

(58) Field of Classification Search .............. 435/4, 435/6, 7.1, 283.1
See application file for complete search history.

(56) References Cited

U.S. PATENT DOCUMENTS

| | | | | |
|---|---|---|---|---|
| 5,306,644 | A | * | 4/1994 | Myerholtz et al. .......... 436/149 |
| 5,352,582 | A | * | 10/1994 | Lichtenwalter et al. ........ 435/6 |
| 5,807,758 | A | * | 9/1998 | Lee et al. .................... 436/526 |
| 6,197,503 | B1 | * | 3/2001 | Vo-Dinh et al. ................ 435/6 |
| 6,278,231 | B1 | * | 8/2001 | Iwasaki et al. .............. 313/310 |
| 6,916,614 | B1 | * | 7/2005 | Takenaka et al. ............... 435/6 |
| 2002/0137083 | A1 | * | 9/2002 | Kobori et al. .................. 435/6 |
| 2003/0089899 | A1 | * | 5/2003 | Lieber et al. .................... 257/9 |
| 2003/0132461 | A1 | * | 7/2003 | Roesner et al. ............. 257/213 |
| 2003/0178617 | A1 | * | 9/2003 | Appenzeller et al. .......... 257/20 |
| 2004/0127637 | A1 | * | 7/2004 | Hsu et al. ................... 524/800 |
| 2004/0200734 | A1 | * | 10/2004 | Co et al. .................. 205/777.5 |
| 2004/0235016 | A1 | * | 11/2004 | Hamers et al. ................. 435/6 |

* cited by examiner

*Primary Examiner*—B J Forman
*Assistant Examiner*—Narayan K Bhat
(74) *Attorney, Agent, or Firm*—H.C. Park & Associates, PLC

(57) ABSTRACT

The present invention is related to a biochip and a biomolecular detection system using the same. In particular, the biomolecular detection system is capable of detecting biological molecules (biomolecules) such as DNA or protein at a high speed. The biochip comprises a supporting structure, conductive materials aligned vertically on, and associated with, the supporting structure, and biomolecule probes operably linked to the conductive materials. The biomolecular detection system using the biochip may precisely detect biomolecules as well as the density of the biomolecules.

16 Claims, 7 Drawing Sheets

BIOCHIP AND BIOMOLECULAR DETECTION SYSTEM USING THE SAME

CROSS-REFERENCE TO RELATED APPLICATIONS

This application claims the priority to Korean Patent Application No. 10-2004-0009837, filed on Feb. 14, 2004, in the Korean Intellectual Property Office, the disclosure of which is incorporated herein in its entirety by reference.

FIELD OF THE INVENTION

The present invention is related to a biochip and a biomolecular detection system using the same. In particular, the present invention is related to a biomolecular system for detecting biological molecules such as DNA or protein. More specifically, the present invention is related to a biochip, comprising a high density of biomolecular probes operably linked to carbon nanotubes or nanowires, which are vertically arranged and associated with a supporting structure, such as a thin film transistor. The biochip is capable of sensing target DNA at a high speed. Additionally, the present invention is related to a biomolecular detection system using the biochip.

BACKGROUND

Many contemporary methods of molecular biology, including nucleic acid hybridization analysis and protein binding analysis, utilize "biochips" or arrays of probe biomolecules ("probes") to bind and detect target biological species ("targets") in complex sample systems. Most commonly in these methods, a sample is simply placed onto the surface of the array and targets contained in the sample passively diffuse toward and bind with the probes immobilized on the support. A fusion of biotechnology, nanotechnology, and micro electro mechanical system (MEMS) technology has led to new technology. For example, biochips and DNA chips have been developed, and are being commercialized in an array formation.

Recently, the concept of Lab-on-a-Chip (LOC) has been introduced to integrate all processes performed in labs into a biochip. The processes include pre-treatment, derivatization, separation, detection, and analysis of various samples such as biological samples, e.g., blood, urine, cells, or saliva, natural substances, chemicals, food, or medicines. DNA-LOCs and protein-LOCs, into which all these lab processes are integrated, are being developed.

Moreover, a carbon nanotube has been used as a major component of a miniaturized cathode-ray tube and applied in various fields. For example, carbon-based nanotubes may be used to fabricate nano-sized microscopy probes. Also, stable iodine-doped carbon nanotubes have been fabricated by doping carbon nanotubes with iodine and fabricated nano-sized metallic nanoscale fibers.

In addition, electrochemiluminescent ruthenium complexes using functional group biomolecule-modified nanotubes have been fabricated. Also, carbon nanotubes have been used in developing high-density and large-capacity biosensors.

A conventional biochip may be fabricated by synthesizing a single strand of DNA on a desired region of a substrate or by spotting a pre-manufactured single or double strand of DNA on a predetermined region of a substrate. However, there is a high possibility that the biomolecular probes to be attached will be aligned randomly on the substrate. Furthermore, the density of the biomolecular probes in a region of the substrate where the biomolecular probes hybridize may be low. Therefore, it is difficult to analyze target DNA precisely.

SUMMARY OF THE INVENTION

The present invention is directed to a biochip comprising a high density of biomolecular probes, which are capable of detecting target biomolecules. Additionally, the present invention is directed to a biomolecular detection system using the biochip.

An aspect of the present invention is directed to a biochip comprising a supporting structure, a plurality of a conductive material spatially distributed over, and stably associated with, the surface of a substantially planar substrate, and where a plurality of biomolecular probes, which are capable of hybridizing to target biomolecules, extend from the conductive material. The conductive materials may be carbon nanotubes or nanowires, which are baton-shaped metallic conductive materials. Furthermore, at least one hole may be formed in the supporting structure and the conductive materials may extend vertically at a specific angle from the at least one hole.

The target biomolecules may be, as described below, any nucleic acid, protein, is peptide, cell, glycoprotein, or polysaccharide that is capable of hybridizing with the biomolecular probes. The biochip may further include microfluidic channels formed on top surfaces of the conductive materials on the supporting structure.

The supporting structure may comprise a substrate, a gate formed on the substrate, and a first doped region and a second doped region formed on opposite sides of the gate in an upper portion of the substrate. The conductive materials may be formed on the first doped region or the second doped region.

Another aspect is a biomolecular detection system employing the biochip of the present invention. The biomolecular detection system is capable of detecting whether the target biomolecules have hybridized to the biomolecular probes. In a further aspect, the system may include a voltage source in order to apply a potential to the conductive materials and a means for determining whether the target molecules have hybridized to the biomolecular probes. In a particular aspect, this may be accomplished by measuring the capacitances between the biomolecular probes and the conductive materials, respectively.

The system may further include a laser generator capable of irradiating a laser beam onto the biomolecular probes or the conductive materials and a detector for identifying whether the target biomolecules have hybridized to the biomolecular probes. The laser beam is irradiated on the conductive materials or the biomolecular probes following a hybridization reaction. The optical signal generated by the biomolecular probes or the conductive materials is then measured. In an alternative aspect, the system of the present invention may include an electrical signal detector for identifying whether the target biomolecules have hybridized to the biomolecular probes. Following the hybridization reaction, the conductive materials or the biomolecular probes may be irradiated with the laser beam and the resultant electrical signals may then be measured.

In yet a further aspect, the system may include a laser generator capable of irradiating a laser beam onto a lower portion of the biochip and a detector for identifying whether the target biomolecules have hybridized to the biomolecular probes. Following the hybridization reaction, the optical signals generated by the lower portion of the biochip by the laser beam may be measured. Moreover, the system may include an electrical signal detector for identifying whether the target biomolecules are attached to the biomolecular probes. The electrical signals generated by the lower portion of the biochip from the laser beam may be measured.

In another aspect, the system of the present invention may include an electromagnetic field generator capable of applying an electromagnetic field to the upper and the lower portion of the biochip and an electrical signal detector for identifying whether the target biomolecules have hybridized to the biomolecular probes. The electrical signals subsequently produced by the conductive materials or the biomolecular probes in response to the electromagnetic fields may then be measured.

The supporting structure may include a piezoelectric substrate. The piezoelectric substrate may further comprise a signal input unit formed on one side of the piezoelectric substrate capable of inputting signals, and a signal output unit formed on the other side of the piezoelectric substrate capable of sensing changes in the signals caused when the target biomolecules hybridize to the biomolecular probes. The supporting structure may also include a hologram material. Furthermore, the supporting structure may also include a light irradiator capable of irradiating an object beam and a reference beam onto the biochip, and an electrical signal detector capable of sensing changes in the electrical signals when the biomolecules hybridize to the biomolecular probes.

DETAILED DESCRIPTION OF THE INVENTION

Figure 1A:
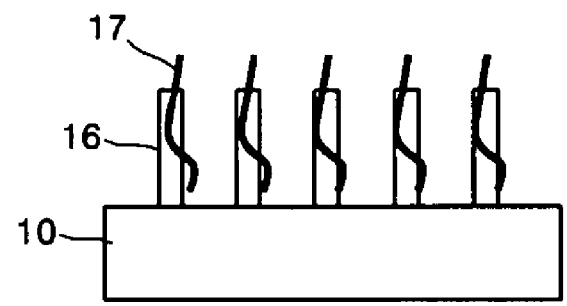
FIG. 1A is a sectional view of a biochip according to an embodiment of the present invention.

It is understood that the present invention is not limited to the particular methodology, protocols, vectors and reagents, etc., described herein, as these may vary. It is also to be understood that the terminology used herein is used for the purpose of describing particular embodiments only, and is not intended to limit the scope of the invention. It must be noted that as used herein and in the appended claims, the singular forms "a," "an," and "the" include the plural reference unless the context clearly dictates otherwise. This, for example, a reference to "a nanotube" or "a nanowire" is a reference to one or more nanotubes or nanowires and equivalents thereof known to those skilled in the art.

Unless defined otherwise, all technical and scientific terms used herein have the same meanings as commonly understood by one of ordinary skill in the art to which this invention belongs. Particular methods, devices, and materials described, although any methods and materials similar or equivalent to those described herein can be used in the practice or testing of the present invention. All references cited herein are incorporated by reference herein in their entirety.

DEFINITIONS

Target biomolecule: for the purposes of the specification and claims refers to a molecule of an organic or inorganic nature, the presence and/or quantity of which is being tested for; and which contains a molecular component (e.g., ligand or sequence or epitope or domain or portion or chemical group or reactive functionality or determinant) for which a biomolecular probe has binding specificity.

Biomolecules: broadly defined, any biological molecule, such as a nucleic acid, molecule, protein, glycoprotein, eukaryotic cell, prokaryotic cell, lipoprotein, peptide, carbohydrate, lipid, phospholipid, aminoglycan, chemical messenger, biological receptor, structural component, metabolic product, enzyme, antigen, drug, therapeutic, toxin, organic chemical, a substrate, and the like. The biomolecule may be in vivo, in vitro, in situ, or ex vivo.

Biomolecular probe: for purposes of the specification and claims, refers to a molecule which has binding specificity and avidity for a molecular component of, or associated with, a target biomolecule. In general, biomolecular probes are known to those skilled in the art to include, but are not limited to, lectins or fragments (or derivatives) thereof which retain binding function, monoclonal antibodies ("mAb", including chimeric or genetically modified monoclonal antibodies), peptides, aptamers, and nucleic acid molecules. Oligonucleotide analogs, backbone modified oligonucleotide analogs, and morpholino-based polymers can be made using methods described in U.S. Pat. Nos. 5,969,135, and 5,596,086, U.S. Pat. Nos. 5,602,240, and 5,034,506, respectively.

Operably linked or operably bonded: for purposes of the specification and claims refers to fusion or bond or an association, of sufficient stability. The bond or link may be for the purposes of signal amplification and detection according to the present invention, between a combination of different molecules such as, but not limited to, between a linker and a biomolecular probe, between an amino acid and a biomolecular probe; and a combination thereof. As known to those skilled in the art, and as will be more apparent by the following embodiments, there are several methods and compositions in which two or more molecules may be operably linked utilizing reactive functionalities. Reactive functionalities include, but are not limited to, bifunctional reagents/linker molecules, biotin, avidin, free chemical groups (e.g., thiol, or carboxyl, hydroxyl, amino, amine, sulfo, etc.), and reactive chemical groups (reactive with free chemical groups).

Linker: for purposes of the specification and claims refers to a compound or moiety that acts as a molecular bridge to operably link two different molecules, wherein one portion of the linker is operably linked to a first molecule, and wherein another portion of the linker is operably linked to a second molecule. The two different molecules may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers may include, but are not limited to, homo-bifunctional linkers and hetero-bifunctional linkers. Heterobifunctional linkers, well known to those skilled in the art, contain one end having a first reactive functionality to specifically link a first molecule, and an opposite end having a second reactive functionality to specifically link to a second molecule. As illustrative examples, to operably link a hydroxyl group of a polynucleotide strand to the amino group of a molecular probe, the linker may have: a carboxyl group to form a bond with the polynucleotide strand, and a carboxyl group to form a bond with the biomolecular probe; or a carboxyl group to form a bond with the polynucleotide strand, and an aldehyde group to form a bond with the biomolecular probe; or a carboxyl group to form a bond with the polynucleotide strand, and a halide group to form a bond with the biomolecular probe. A linker may comprise a primary amine reactive group to react with an amino acid (e.g., lysine) residue of a molecular probe comprising a mAb, and a thiol reactive group to react with a terminally thiolated polynucleotide strand. Heterobifunctional photo-reactive linkers (e.g., phenylazides containing a cleavable disulfide bond) are known in the art. For example, a sulfo-succinimidyl-2-(p-azido salicylamido) ethyl-1,3'-dithiopropionate contains a N-hydroxy-succinimidyl group reactive with primary amino groups, and the phenylazide (upon photolysis) reacts with any amino acids. The linker may further comprise a protective group which blocks reactivity with a functional group on the linker which is used to react with and bind to a molecule to be linked. A deprotection reaction may involve contacting the linker to one or more conditions and/or reagents which removes the protective group, thereby exposing the functional group to interact with the molecule to be linked. Depending on the nature of the protective group, deprotection can be achieved by various methods known in the art, including, but not limited to photolysis, acidolysis, hydrolysis, and the like. Depending on such factors as the molecules to be linked, and the conditions in which the method of detection is performed, the linker may vary in length and composition for optimizing such properties as flexibility, stability, and resistance to certain chemical and/or temperature parameters. For example, short linkers of sufficient flexibility include, but are not limited to, linkers having from 2 to 10 carbon atoms (see, e.g., U.S. Pat. No. 5,817,795).

Polypeptide: a sequence of amino acids, peptides, fragments of polypeptides, proteins, globular proteins, glycoproteins, and fragments thereof.

Hybridization: broadly defined, any process by which a nucleic acid sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency. In particular, stringency can be increased by reducing the concentration of salt, increasing the concentration of formamide, or raising the hybridization temperature. For example. Hybridization under high stringency conditions could occur in about 50% formamide at about 37° C. to about 42° C. Hybridization could occur under reduced stringency conditions in about 35% to about 25% formamide at about 30° C. to about 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of about 35° C. This temperature range corresponding to a particular level of stringency can be further narrowed by calculating the purine to pyrimidine ration of the nucleic acid of interest and adjusting the temperature accordingly. Variations on the above ranges and conditions are well known in the art.

Effective amount: as used herein, refers to an amount of a molecule or compound sufficient to contact and operably link its target for which it has binding specificity (if present in the mixture) for the purposes of signal amplification and detection according to the present invention.

Isolated: as used herein, refers to any element or compound separated not only from other elements or compounds that are present in the natural source of the element or compound, but also from other elements or compounds and, as used herein, specifically refers to an element or compound found in the presence of only a solvent, buffer, ion, or other component normally present in a solution.

Nucleic acid sequences: includes an oligonucleotide, nucleotide, or polynucleotide, and fragments thereof, and to DNA or RNA of genomic, recombinant, or synthetic origin which may be single- or double-stranded, and represents the sense or antisense strand, to peptide nucleic acid (PNA), or to any DNA-like or RNA-like material, natural or synthetic in origin.

Amino acid sequence: as used herein, this term includes an oligopeptide, peptide, polypeptide, or protein sequence, and fragment thereof, and to naturally occurring or synthetic molecules.

Sample: is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention.

Fragments: includes any portion of a heterologous peptide or nucleic acid sequence. Heterologous peptide fragments retain at least one structural or function characteristic of the subject heterologous polypeptide. Nucleic acid sequence fragments are greater than about 60 nucleotides in length, and in particular, include fragments that are at least about 100 nucleotides, at least about 1000nucleotides, and at least about 10,000 nucleotides in length.

Complementary or complementarity: as used herein, include the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acid binds, or it may be complete when total complementarity exists between the single-stranded molecules. The degree of complementarity between nucleic acid strands has significant effects on the efficiency and strength of hybridization between nucleic acid strands.

% similarity or % identity: refer to the percentage of sequence similarity or identity found in a comparison of two or more amino acid or nucleic acid sequences. Percent similarity can be determined by methods well-known in the art. For example, percent similarity between amino acid sequences can be calculated by using the clustal method. The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, time one hundred. Gaps of low or of no homology between the two amino acid sequences are not included in determining percentage similarity. Percent similarity can be calculated by other methods known in the art, for example, by varying hybridization conditions, can be calculated electronically using programs such as MEGALIGN™ program (DNAS-TAR Inc, Madison, Wis.).

Biochip: refers to a plurality of conductive materials vertically and spatially distributed over, and stably associated with, the surface of a substantially planar substrate, and extending therefrom, a plurality of biomolecular probes. The biochip of the present invention refers to microfabricated array of conductive materials and extending therefrom, a plurality of different biomolecular probes that can effectively be used to not only detect the presence or absence of target biomolecules, but to quantify the relative abundance of the target biomolecules in a complex biomolecule pool. The biomolecular probes are complementary to the biomolecule targets and can quantify the hybridized biomolecules in the array.

Conductive materials: refers to any carbon nanotube or nanowire, which may be a metallic conductive material having an arbitrary shape. In a specific embodiment, the nanowire or nanotube of the present invention has a baton shape. There is no specific limitation on the species of nanotube or nanowire to be used by the methodologies of the present invention or in the biochip of the present invention. Generally, examples of nanotubes or nanowires include those comprising metals, metal oxides, inorganic materials, organic materials, or mixtures thereof, all of which may have arbitrary shapes. For example, this material can be a metal such as gold, silver, palladium, or copper, a semiconductor such as an elemental semiconductor (such as silicon or germanium) or a compound semiconductor (such as GaAS or CdS), a metal compound such as titanium oxide, tin oxide, or another metal oxide, or a chalcogenide, or another known substance. The nanotubes or nanowires of the present invention may be uniformly or spatially oriented on the substrate.

Optical detector, photodetector, or electrical signal detector: refers to a device that generates an output signal when irradiated with optical energy. Thus, in its broadest sense the term detector system is taken to mean a device for converting energy from one form to another for the purpose of measurement of a physical quantity or for information transfer. Optical detectors include but are not limited to photomultipliers and photodiodes.

Processor: refers to a device that performs a set of steps according to a program (e.g., a digital computer). Processors, for example, include Central Processing Units ("CPUs"), electronic devices, or systems for receiving, transmitting, storing and/or manipulating digital data under programmed control.

Referring to FIG. 1A, the biochip may comprise a supporting structure 10 composed of an insulating or semiconductive material, a plurality of carbon nanotubes 16 (or conductive materials such as nanowires), each grown vertically from the supporting structure 10, and a plurality of biomolecular probes 17 extending from the carbon nanotubes 16, respectively.

Figure 1B:
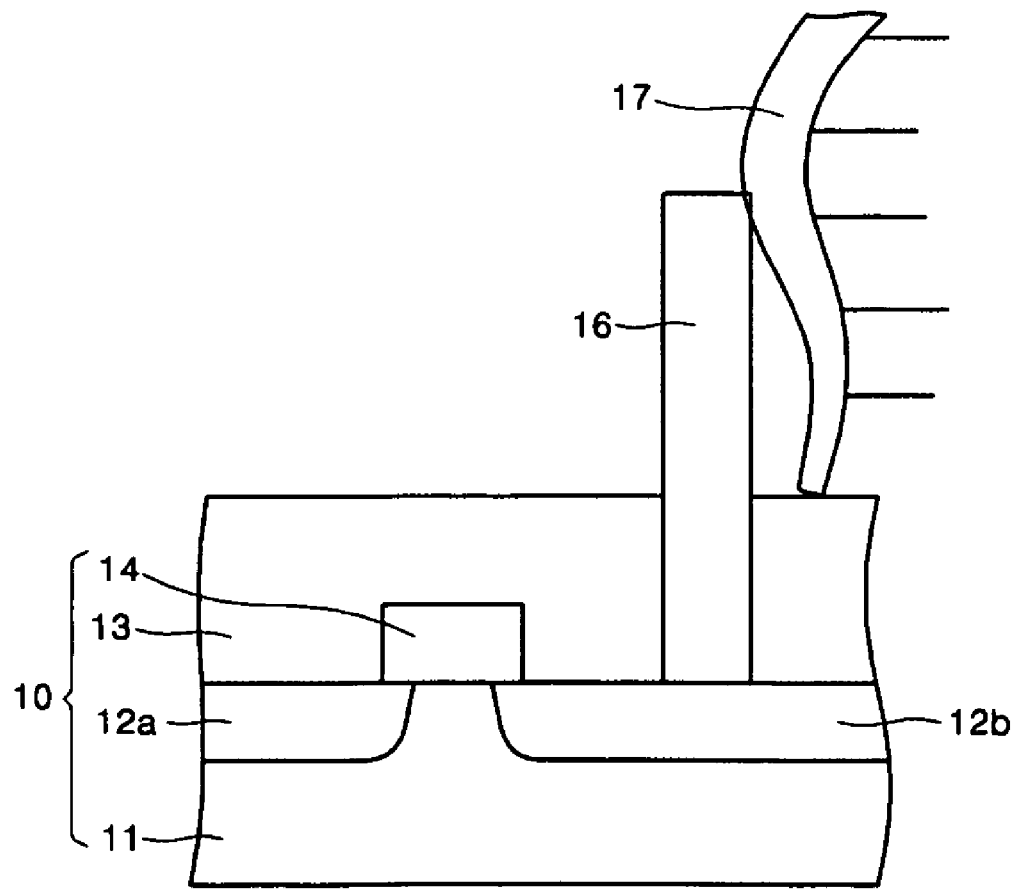
FIG. 1B is an enlarged sectional view of an enlarged sectional view of the biochip illustrated in FIG. 1.

Referring to FIG. 1B, each of the carbon nanotubes 16 is connected to a first doped region 12a or a second doped region 12b of a thin film transistor (TFT) formed on a substrate 11. In other words, the supporting structure 10 may be a TFT structure. When the supporting structure 10 is the TFT structure, each of the carbon nanotubes 16 may be electrically connected to the first doped region 12a or the second doped region 12b of the TFT structure and the biomolecular probes 17 may be operably linked to the carbon nanotubes 16. The TFT may include the first doped region 12a and the second doped region 12b formed by doping the substrate 11, which may be a silicon substrate, with predetermined impurities, and a gate 14 formed between the first and the second doped regions 12a and 12b on the substrate 11.

The TFT may be easily fabricated using a conventional semiconductor fabrication process. Briefly, the substrate 11 is first prepared. Then, a material constituting the gate 14 is deposited on the substrate 11, and the material may be etched to form the gate 14 such that portions of the substrate 11 are exposed. Then, a predetermined material is doped into the exposed portions of the substrate 11 on both sides of the gate 14 to form the first doped region 12a and the second doped region 12b.

An insulating layer 13 may be formed by depositing $Al_2O_3$ or an oxide on the substrate 11 and the gate 14. This process is similar to a conventional transistor fabrication process. The insulating layer 13 may be etched to expose the first doped region 12a or the second doped region 12b, thereby forming a plurality of holes in the biochip. The carbon nanotubes 16 may be grown vertically or at a specific angle from the holes using a thermal CVD process or a PECVD process.

Figure 2A:
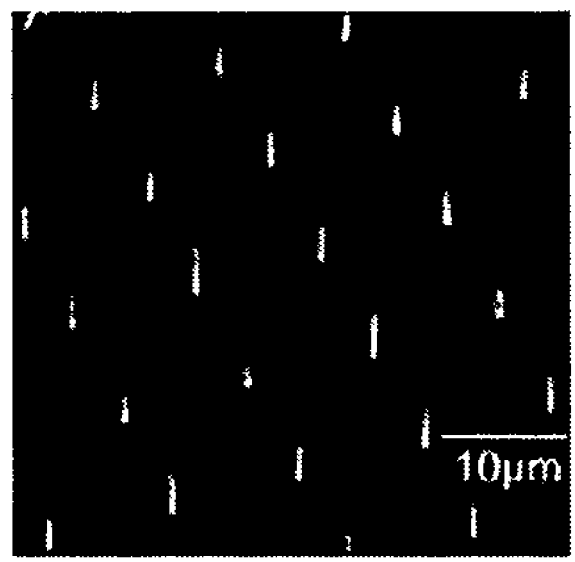
FIGS. 2A, 2B, 2C and 2D illustrate the formation of a plurality of carbon nanotubes disposed vertically on a supporting structure along with biomolecular probes hybridized to target biomolecules.
Figure 2A:
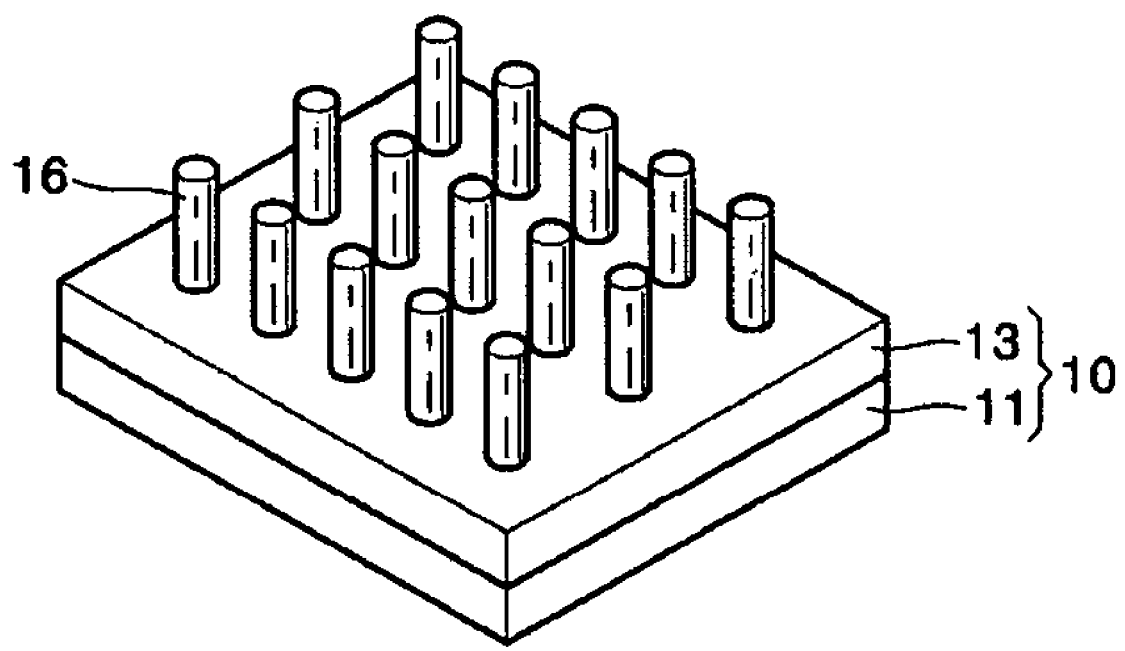

Referring to FIG. 2A, after forming an array of TFTs, the carbon nanotubes 16 may be arranged vertically on the TFT array. The carbon nanotubes 16 may be electrically connected to the first doped regions 12a or the second doped regions 12b of the respective TFTs disposed below the carbon nanotubes 16.

Figure 2B:
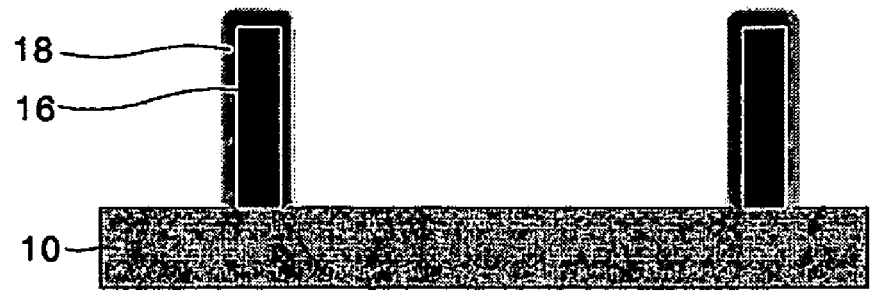

Referring to FIG. 2B, functional materials 18, i.e., linker compounds, which may be functionalized with groups, such as amino groups, are coated onto surfaces of the carbon nanotubes 16. The biomolecular probes 17, which are already synthesized, may be operably linked to the functional materials 18 of the carbon nanotubes 16. In this process, a piezoelectric method, such as a direct contact method or an ink jet method, or an electrical method may be used.

The biochip according to an embodiment of the present invention may be easily fabricated using the above method. Since the biomolecular probes 17 may be operably linked to the carbon nanotubes 16 (or the nanowires), the density of the biomolecular probes 17 may be increased by improving the degree of integration of the TFTs.

A biomolecular detection system for detecting biomolecules such as nucleic acid molecules, proteins, peptides, glycoproteins, carbohydrates, or polysaccharides, for example, may employ the biochip of the present invention. In a particular embodiment, the biomolecular detection system may be used to analyze hybridization reactions, protein/nucleic acid binding reactions, enzymatic reactions, and the like. Furthermore, the biomolecular detection system may be used to detect the binding of arrayed peptides to potential binding partners (e.g., other peptides, nucleic acids, lipids, receptor binding factors, hormones, drugs, co-factors, etc.) For nucleic acid, peptide and other types of biochips, the biomolecular detection system may be used for screening assays (e.g., drug screening assays). For example, a candidate compound (e.g., a drug) suspected of having biological activity in the presence of another agent can be exposed to a biochip comprising the agent to determine if there in an interaction. Such screening methods can, for example, determine the ability of compounds to prevent the binding of two other agents to one another by detecting the presence or absence of binding complexes in the presence of the compound.

In embodiments where nucleic acids (e.g., DNA) comprise the biomolecular probes, a hybridization step is typically carried out to bind a target biomolecule, either labeled or unlabeled, to the biomolecular probes. More generally, the biomolecular probes are used to determine the existence and or the extent of appearance of a particular complementary molecule in a sample contacted to the biochip and its biomolecular probe. Typically the biomolecular probes bound to the biochip themselves interact with binding partners when contacted with a solution containing a sample.

For illustrative purposes only, the biomolecular detection system of the present invention will be described using DNA as the biomolecule since it is relatively easy to analyze. According to an embodiment of the present invention, the biomolecular probes 17 (DNA probes) are operably linked to the nanotubes vertically arranged on the biochip. The DNA probes are first contacted with an effective amount of the target DNA to be analyzed under conditions for the biomolecular probe to bind to the target DNA, if present. The particular hybridization reaction conditions can be controlled to alter hybridization (e.g., increase or decrease oligonucleotide binding stringency). For example, reaction temperature, concentrations of anions and cations, addition of detergents, and the like, can all alter the hybridization characteristics of biomolecular probe and target biomolecules.

Figure 2C:
Figure 2D:
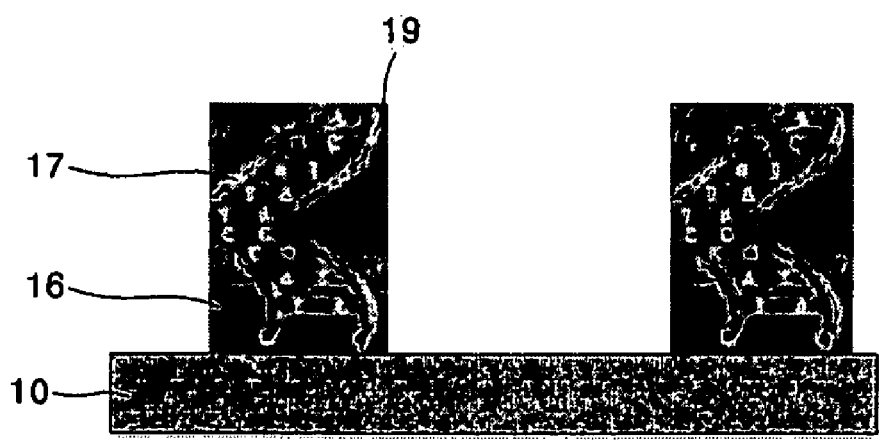

In a further embodiment, one or more wash steps after the initial contact of the probe with the target DNA to remove unbound sample or non-specifically bound sample may be employed. Following the hybridization reaction, the biomolecular detection system measures the density of target DNA with a specific DNA sequence in each DNA sample bound to the biomolecular probes (FIG. 2C).

Figure 3:
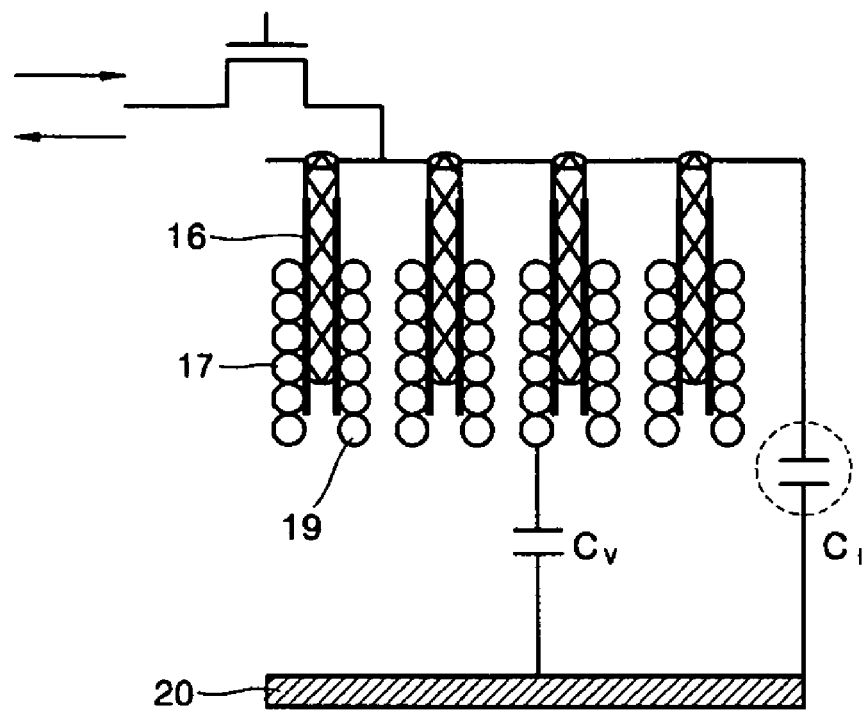
FIG. 3 illustrates a biomolecular detection system electrically measuring changes in an amount of electric charges in accordance with whether target DNA and biomolecular probes are hybridized according to an embodiment of the present invention.

FIG. 3 illustrates a biomolecular detection system for determining whether the target DNA 19 and the DNA probes 17, which are operably linked to carbon nanotubes 16, have hybridized by electrically measuring a change in the number of electric charges. Referring to FIG. 3, the carbon nanotubes 16 electrically connected with reference 20 are formed in the second doped region 12b of FIG. 1A, with the biomolecular probes 17 operably linked to the carbon nanotubes 16. When a predetermined voltage is applied to carbon nanotubes, a capacitor C1 is charged with positive voltage.

When a DNA (target DNA 19) sample is put in contact with the biochip, the target DNA 19 hybridizes with the complementary biomolecular probes 17 through hydrogen bonding. The hybridized DNA is charged to a negative voltage, and the voltage applied to C1 is applied to Cv and the carbon nanotubes 16. The value of Cv is obtained by a change in capacitance between the carbon nanotubes 16 and the hybridized DNA. Therefore, it is possible to read a change in the capacitance and, based on the change in the capacitance, analyze the density of the hybridized DNA in the biochip with the array structure. A separate differential amplifier (not shown) is prepared to measure a change in the value of Cv. The size of the change in the value of Cv or a difference between C1 and Cv may be amplified before being analyzed.

Figure 4A:
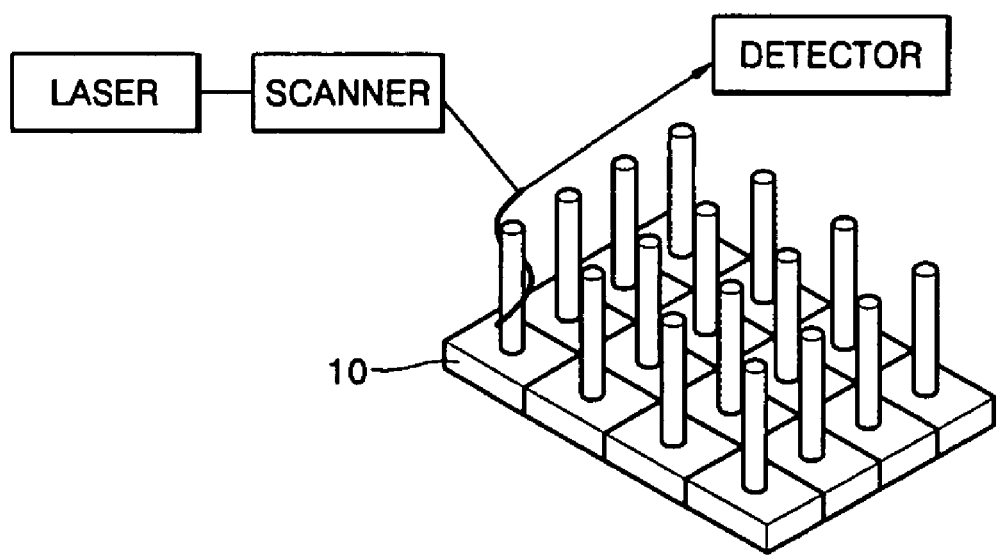
FIGS. 4A, 4B and 4C illustrate biomolecular detection systems analyzing a density of hybridization of biomolecular probes and target DNA by irradiating a laser beam onto a biochip according to embodiments of the present invention.
Figure 4B:
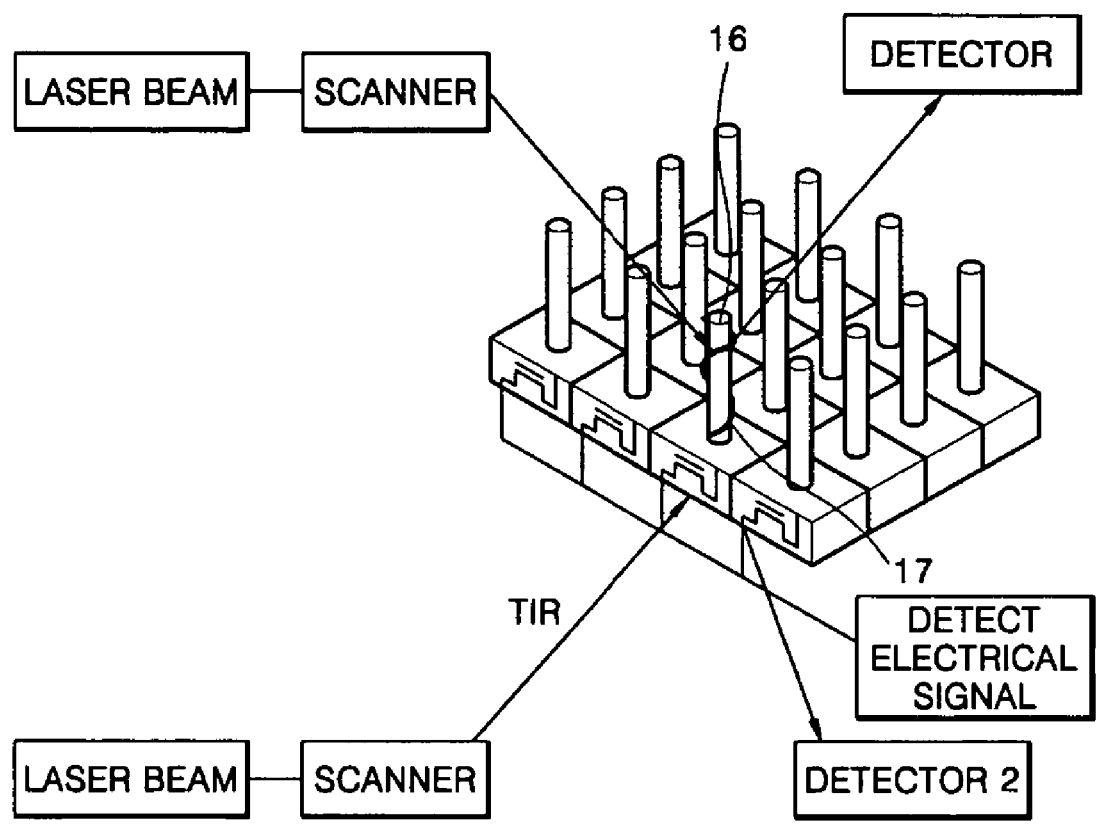
Figure 4C:
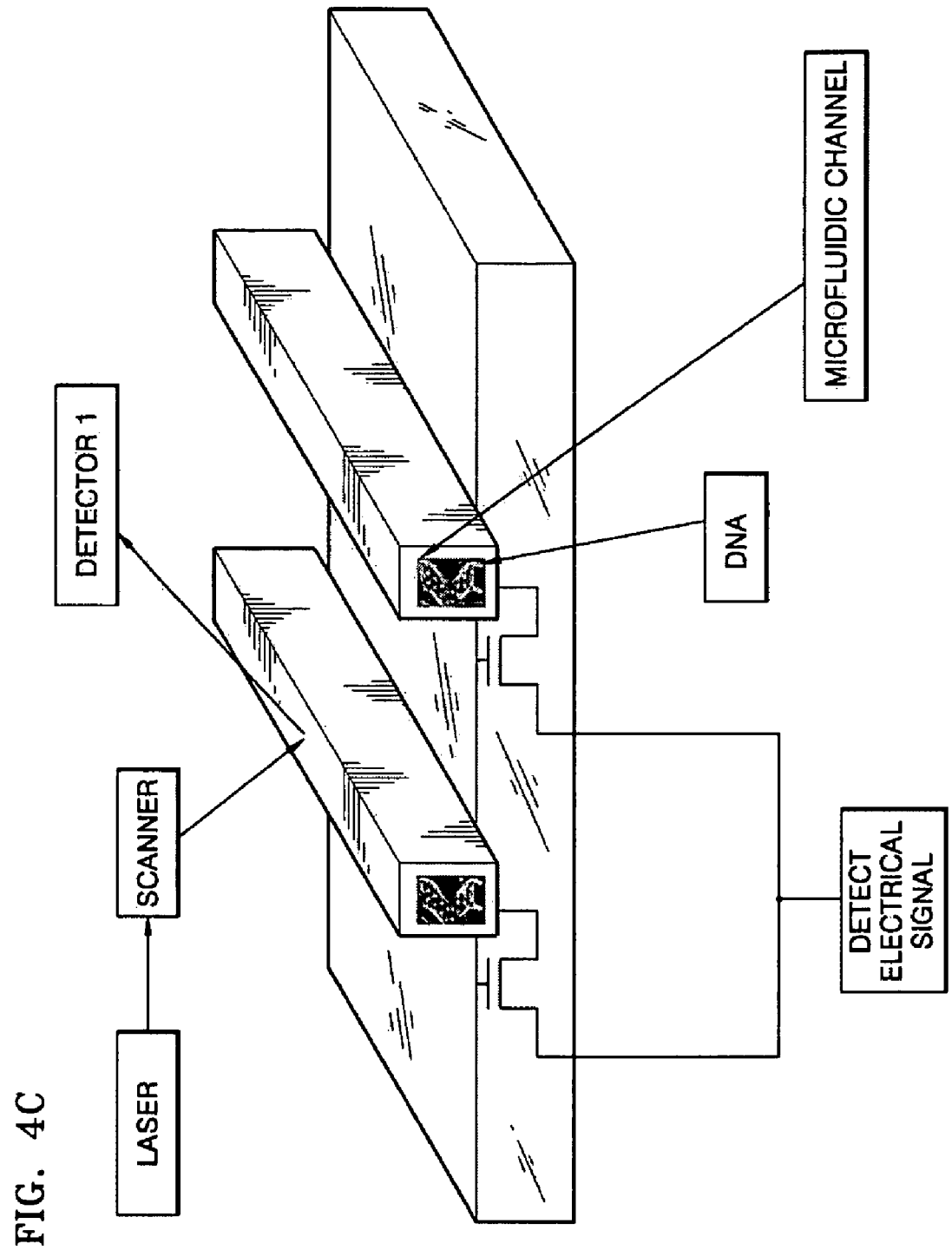

FIGS. 4A through 4C, which illustrate an embodiment of the present invention, show a biomolecular detection system capable of analyzing a density of hybridization of probe molecules 17 and target DNA 19 by irradiating a laser beam onto the biochip. Referring to FIG. 4A, a laser beam with a predetermined wavelength may be generated by a laser beam generator. The laser beam may be irradiated onto each biomolecular probe 17 formed on each carbon nanotube 16 in each unit cell of the biochip by a high-speed X-Y scanner. Optical signals detected by detectors in the unit cells are input to a processor (not shown). When the laser beam is irradiated onto the hybridized DNA, electrical signals may be detected in the respective unit cells by electrodes connected to the carbon nanotubes 16, i.e., conductors.

If a DNA sample to be analyzed is put in contact with the biochip, the target DNA 19 within the DNA sample is hybridized with the biomolecular probes 17. To determine whether the target DNA 19 and the biomolecular probes 17 are hybridized in each unit cell of the biochip, a laser beam with the same wavelength as the laser beam initially irradiated is irradiated on the hybridized DNA. If the target DNA 19 and the biomolecular probes 17 are hybridized, an optical signal detected by the detector after the hybridization is different from the optical signal detected before the hybridization. By measuring this difference for each unit cell of the biochip, it is possible to determine whether the biomolecular probes 17 and the target DNA 19 are hybridized. Accordingly, it is possible to detect the target DNA 19 and its density.

FIG. 4B illustrates a biomolecular detection system detecting an optical signal output from each unit cell of the biochip using an external detector or detecting an electrical signal by irradiating a laser beam onto a lower portion of the biochip. The biomolecular detection system includes a laser beam generator disposed in a lower portion of a substrate that irradiates a laser beam onto each unit cell of the biochip at an angle close to a total reflection angle of the substrate. An electrical signal generated by the laser beam may be measured before and after the hybridization. Therefore, it is possible to determine whether the biomolecular probes 17 and the target DNA 19 are hybridized in each unit cell of the biochip and analyze the density of the hybridized DNA in the entire biochip array more precisely.

FIG. 4C illustrates a biomolecular detection system including microfluidic channels formed on a biochip and biomolecular probes 17 respectively attached to carbon nanotubes 16 in the microfluidic channels. When fabricating the biochip in an array formation, a functional material may be coated onto the carbon nanotubes 16. Then, glass with a channel structure is aligned and fixed in a desired region. The biochip array with this channel structure may be very useful for analyzing various kinds of biomolecules.

If there are various types of target DNA 19, a channel region is formed for each type of the target DNA 19, and the biomolecular probes 17 appropriate for each type of the target DNA 19 may be attached to the carbon nanotubes 16 of the appropriate channel region and analyzed. In other words, in the case of the biochip in the array formation, the biomolecular probes 17 attached to the carbon nanotubes 16 may be identical. Alternatively, as illustrated in FIG. 4C, microfluidic channels may be formed, and the biomolecular probes 17 attached to the carbon nanotubes 16 may be different from one another to measure the density of hybridization according to type of target DNA.

The target DNA 19 may be injected at one end of a microfluidic channel by a capillary phenomenon or moved inside the microfluidic channel by applying an electric field to both ends of the microfluidic channel. As in the biomolecular detection system illustrated in FIG. 4A, the biomolecular detection system illustrated in FIG. 4C irradiates a laser beam onto a top portion of a substrate to generate and measure optical signals or electrical signals in order to determine the intensity of the hybridization. However, either of the biomolecular detection systems of FIG. 3 and FIG. 4B may be used.

Figure 5:
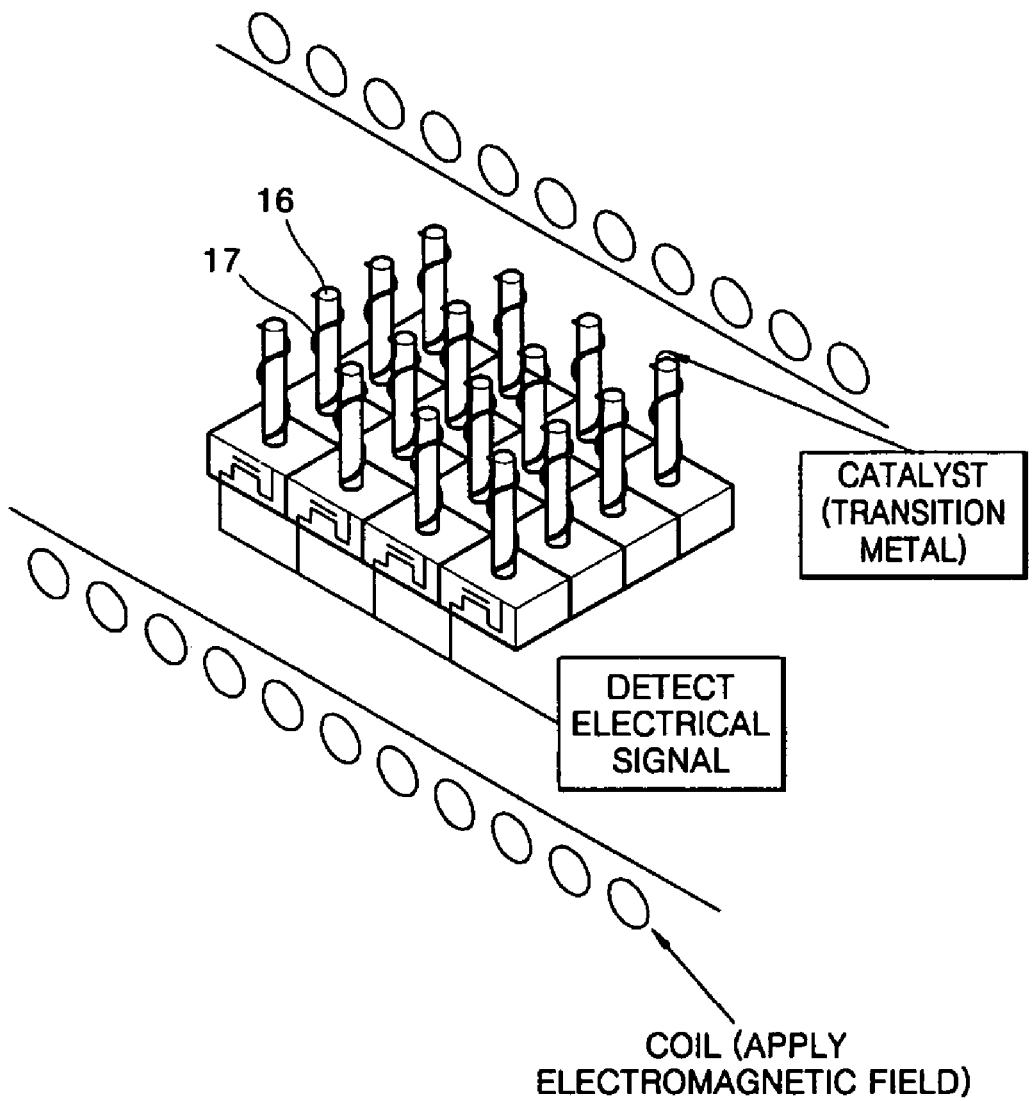
FIG. 5 illustrates a detection system according to an embodiment of the present invention analyzing the density of hybridization by attaching a catalyst, such as a transition metal, to an end of each carbon nanotube of a biochip according to an embodiment of the present invention or by applying an external electromagnetic field to each of the carbon nanotubes including the catalyst.

FIG. 5 illustrates a detection system according to an embodiment of the present invention analyzing the density of hybridization by attaching a catalyst, such as a transition metal, to an end of each carbon nanotube 16 of a biochip according to an embodiment of the present invention or by applying an external electromagnetic field to each of the carbon nanotubes 16 including the catalyst. Referring to FIG. 5, if the electromagnetic field is applied to a catalyst such as a transition metal, a thermal or electrical signal may be generated by the catalyst. The electrical signal may be transmitted to a conductive electrode of a transistor via the carbon nanotube 16. The electrical signal may be detected by an external electrical signal detector (not shown). Therefore, it is possible to measure the intensity of the hybridization between the target DNA 19 and the biomolecular probes 17.

Specifically, a catalyst, such as a transition metal, may be attached to an end of each of the carbon nanotubes 16, and an electromagnetic field may be applied to the end of each of the carbon nanotubes 16 by an external coil and only the biomolecular probes 17 are operably linked to the ends of the respective carbon nanotubes 16. Then, an electrical signal is detected, and the strength of the electrical signal is set as an initial value before hybridization. When a DNA sample is put in contact with the biochip array, the target DNA and the biomolecular probes 17 are hybridized with the biomolecular probes 17. An electromagnetic field is again applied to the target DNA. Then, the electrical signal is detected, and the strength of the electrical signal is set as a value after the hybridization. By measuring the difference between the initial value of the electrical signal before the hybridization and the value of the electrical signal after the hybridization in each unit cell of the biochip, it is possible to identify whether the target DNA 19 and the probe biomolecule 17 in each of the unit cells are hybridized as well as the intensity of the hybridization in the entire biochip array.

Figure 6:
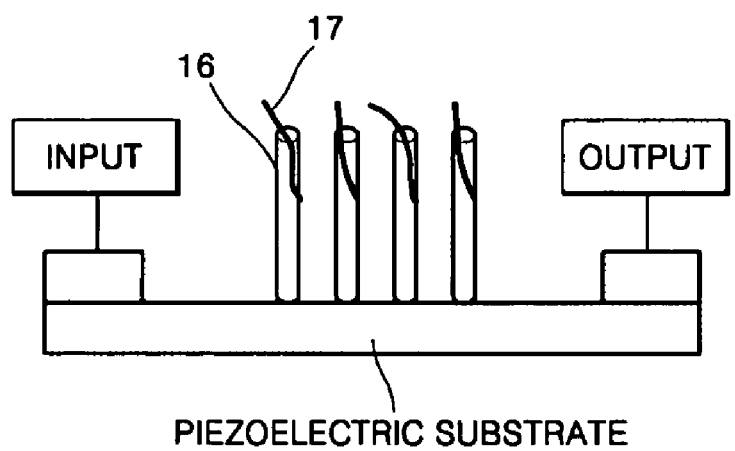
FIG. 6 illustrates a biomolecular detection system detecting whether biomolecular probes and target DNA are hybridized based on a surface acoustic wave according to an embodiment of the present invention.

FIG. 6 illustrates a biomolecular detection system detecting whether biomolecular probes 17 and target DNA 19 are hybridized based on a surface acoustic wave according to an embodiment of the present invention. When fabricating a biochip for use in the present embodiment, holes may be formed in a piezoelectric substrate, and carbon nanotubes 16 may be formed inside the holes. An input line and an output line are formed on opposite sides of the piezoelectric substrate. When an electrical signal is transmitted to the input line, a surface acoustic wave flows along the surface of the piezoelectric substrate and is detected via the output line. In this case, there is a difference between an electrical signal detected via the output line when only the biomolecular probes 17 are operably linked to the carbon nanotubes 16 and the electrical signal detected via the output line when the target DNA 19 is attached to the biomolecular probes 17. By detecting this difference, the biomolecular detection system detects a relative amount of the target DNA 19 attached to the biomolecular probes 17. In this case, instead of being formed in the second doped region 12a of the transistor of FIG. 1, the carbon nanotubes 16 may be formed in the piezoelectric substrate.

In addition, the holes may be formed in a substrate containing a hologram material, and the carbon nanotubes 16 may be grown vertically from the substrate inside the holes. With the biomolecular probes 17 attached to the carbon nanotubes 16, a biochip is formed. After irradiating an object beam and a reference beam on the hybridized DNA, electrical signals are detected before and after the hybridization. By detecting the electrical signals before and after the hybridization, it is possible to measure whether the target DNA 19 and the biomolecular probes 17 in each unit cell of the biochip are hybridized and to measure the density of the hybridization in the biochip array.

The present invention has the following advantages. First, a large number of target biomolecules can be detected by attaching biomolecular probes to several nanosized carbon nanotubes or nanowires. Second, since various biomolecules can be detected in a carbon nanotube or nanowire, it is possible to precisely determine an intensity of biomolecules. Third, various types of biomolecules may be detected simultaneously by forming a plurality of microfluidic channels in the biochip array. Fourth, a reliable detection result may be obtained since biomolecules can be detected in each cell unit in diverse ways.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A biochip, comprising:
a supporting structure;
one or more conductive materials spatially associated with and distributed on the supporting structure; and
one or more biomolecular probes operably linked to the conductive materials,
wherein at least one hole is formed in the supporting structure and the one or more conductive materials extend vertically from the at least one hole,
wherein the one or more biomolecular probes contact vertical surfaces of the conductive materials,
wherein the conductive material is a carbon nanotube or a nanowire, which are baton-shaped metallic conductive materials,
wherein the supporting structure comprises:
a substrate;
a gate formed on the substrate; and
a source and a drain formed on opposite sides of the gate in an upper portion of the substrate, and
wherein the conductive materials are formed on the source or the drain.

2. The biochip of claim 1, further comprising a target biomolecule hybridized to the biomolecular probe.

3. The biochip of claim 2, wherein the target biomolecules are one or more selected from the group consisting of a nucleic acid molecule, a protein, a glycoprotein, a eukaryotic cell, a prokaryotic cell, a lipoprotein, a peptide, a carbohydrate, a lipid, a phospholipid, an aminoglycan, a biological receptor, a structural component, a metabolic product, an enzyme, an antigen, a drug, a therapeutic, a toxin, an organic chemical, and a substrate.

4. A biomolecular detection system comprising the biochip of claim 2, which is capable of detecting whether the target biomolecules are hybridized to the biomolecular probes.

5. The system of claim 4, further comprising:
a voltage source for applying a potential to the conductive materials; and
a measurer for determining whether the target molecules are hybridized to the biomolecular probes by measuring capacitances between the biomolecular probes and the conductive materials.

6. The system of claim 4, further comprising:
a laser generator for irradiating a laser beam onto the biomolecular probes or the conductive materials; and
a detector for detecting whether the target biomolecules are hybridized to the biomolecular probes by measuring optical signals generated by the biomolecular probes or the conductive materials onto which the laser beam was irradiated.

7. The system of claim 6, further comprising an electrical signal detector for detecting whether the target biomolecules are hybridized to the biomolecular probes by measuring electrical signals generated by the biomolecular probes or the conductive materials onto which the laser beam was irradiated.

8. The system of claim 4, further comprising:
a laser generator for irradiating a laser beam onto a lower portion of the biochip; and
a detector for detecting whether the target biomolecules are attached to the biomolecular probes by measuring optical signals generated by the lower portion of the biochip onto which the laser beam was irradiated.

9. The system of claim 8, further comprising an electrical signal detector detecting whether the target biomolecules are attached to the biomolecular probes by measuring electrical signals generated by the lower portion of the biochip onto which the laser beam was irradiated.

10. The system of claim 4, further comprising:
an electromagnetic field generator applying electromagnetic fields to an upper and the lower portion of the biochip; and
an electrical signal detector detecting whether the target biomolecules are hybridized to the biomolecular probes by measuring electrical signals generated by the conductive materials or the biomolecular probes in response to the electromagnetic fields generated by the electromagnetic field generator.

11. The system of claim 4, wherein the supporting structure comprises:
a piezoelectric substrate;
a signal input unit formed in one side of the piezoelectric substrate and inputting signals; and
a signal output unit formed in the other side of the piezoelectric substrate and sensing changes in signals caused by the biomolecular probes becoming hybridized to the target biomolecules.

12. The system of claim 4, wherein the supporting structure contains a hologram material and comprises a light irradiator irradiating an object beam and a reference beam on the biochip and an electrical signal detector sensing changes in electrical signals caused by the biomolecular probes hybridizing to the target biomolecules.

13. The biochip of claim 1, further comprising microfluidic channels formed on top surfaces of the conductive materials on the supporting structure.

14. The biochip of claim 1, wherein the
source comprises a first doped region and the drain comprises a second doped region formed on opposite sides of the gate in the upper portion of the substrate.

15. The biochip of claim 14, wherein the conductive materials are formed on the first doped region or the second doped region.

16. A biochip, comprising:
a supporting structure;
one or more cylindrical conductive materials disposed in respective holes in the supporting structure, the cylindrical conductive materials extending perpendicular to the supporting structure from the respective holes; and
one or more biomolecular probes directly coupled to a surface of each conductive material, the surface extending perpendicular to the supporting structure;
wherein the conductive material is a carbon nanotube or a nanowire,
wherein the supporting structure comprises:
a substrate;
a gate formed on the substrate; and
a source and a drain formed on opposite sides of the gate in an upper portion of the substrate, and
wherein the conductive materials are formed on the source or the drain.

\* \* \* \* \*